United States Patent
Galli et al.

(10) Patent No.: US 10,022,612 B2
(45) Date of Patent: Jul. 17, 2018

(54) SYSTEM FOR MEASURING AND CORRECTING THE FINISH TIME OF AN ATHLETE IN A RACE

(71) Applicant: Swiss Timing Ltd, Corgémont (CH)

(72) Inventors: Reto Galli, Munchenbuchsee (CH); Alexander Kollega, Leipzig (DE); Fabien Masse, Lausanne (CH)

(73) Assignee: Swiss Timing Ltd, Corgémont (CH)

( * ) Notice: Subject to any disclaimer, the term of this patent is extended or adjusted under 35 U.S.C. 154(b) by 0 days.

(21) Appl. No.: 15/359,011

(22) Filed: Nov. 22, 2016

(65) Prior Publication Data
US 2017/0173438 A1    Jun. 22, 2017

(30) Foreign Application Priority Data
Dec. 18, 2015   (EP) ..................................... 15201308

(51) Int. Cl.
*A63F 9/24*     (2006.01)
*A63B 71/06*    (2006.01)
(Continued)

(52) U.S. Cl.
CPC .......... *A63B 71/0605* (2013.01); *A61B 5/002* (2013.01); *A61B 5/1116* (2013.01);
(Continued)

(58) Field of Classification Search
CPC .............. A61B 5/0022; A63B 24/0006; A63B 69/0028; A63B 2024/0025; A63B 71/0605
See application file for complete search history.

(56) References Cited

U.S. PATENT DOCUMENTS 5,103,433 A * 4/1992 Imhof ..................... G07C 1/24
                                                 346/107.2
6,433,817 B1* 8/2002 Guerra .................... G07C 1/24
                                                 348/157
(Continued)

FOREIGN PATENT DOCUMENTS

CH   707 401 A2    6/2014
EP   1 369 146 A1  12/2003

OTHER PUBLICATIONS

European Search Report dated Jun. 23, 2016 in European Application 15201308.2, filed on Dec. 18, 2015 (with English Translation of Categories of cited documents and Written Opinion).

*Primary Examiner* — Steve Rowland
(74) *Attorney, Agent, or Firm* — Oblon, McClelland, Maier & Neustadt, L.L.P.

(57) ABSTRACT

The measuring system makes it possible to correct a finish time for an athlete in a running race. The system comprises a personalized transponder module placed on an upper part of the athlete's body and a base station. The transponder module comprises a signal receiver unit, a data, measurement or command processing unit, and a data and/or measurement and/or command signal transmission unit, and a motion sensor for providing measurement signals to the processing unit. The motion sensor may be a gyroscope connected to the processing unit in the transponder unit and configured to determine an angle of inclination of the athlete's body with respect to a vertical or horizontal direction upon crossing the finish line for correction of the race finish time.

11 Claims, 2 Drawing Sheets

(51) Int. Cl.
    *A63K 3/00*     (2006.01)
    *A61B 5/00*     (2006.01)
    *A61B 5/11*     (2006.01)
    *G07C 1/24*     (2006.01)

(52) U.S. Cl.
    CPC .......... *A61B 5/1121* (2013.01); *A61B 5/6823* (2013.01); *A63B 71/0686* (2013.01); *A63K 3/00* (2013.01); *G07C 1/24* (2013.01); *A61B 2503/10* (2013.01); *A61B 2562/0219* (2013.01); *A63B 2220/40* (2013.01); *A63B 2220/62* (2013.01); *A63B 2220/803* (2013.01); *A63B 2220/836* (2013.01); *A63B 2225/54* (2013.01)

(56) References Cited

U.S. PATENT DOCUMENTS

| | | | | |
|---|---|---|---|---|
| 6,545,705 | B1* | 4/2003 | Sigel ........................ | G07C 1/24 |
| | | | | 348/157 |
| 2005/0237209 | A1* | 10/2005 | Van Dongen ...... | A63B 23/0244 |
| | | | | 340/573.7 |
| 2013/0044043 | A1* | 2/2013 | Abdollahi ............ | A42B 3/0433 |
| | | | | 345/8 |
| 2015/0116497 | A1* | 4/2015 | Doval .................... | G01S 7/412 |
| | | | | 348/157 |
| 2016/0307042 | A1* | 10/2016 | Martin .................... | G07C 1/24 |

* cited by examiner

Fig. 1
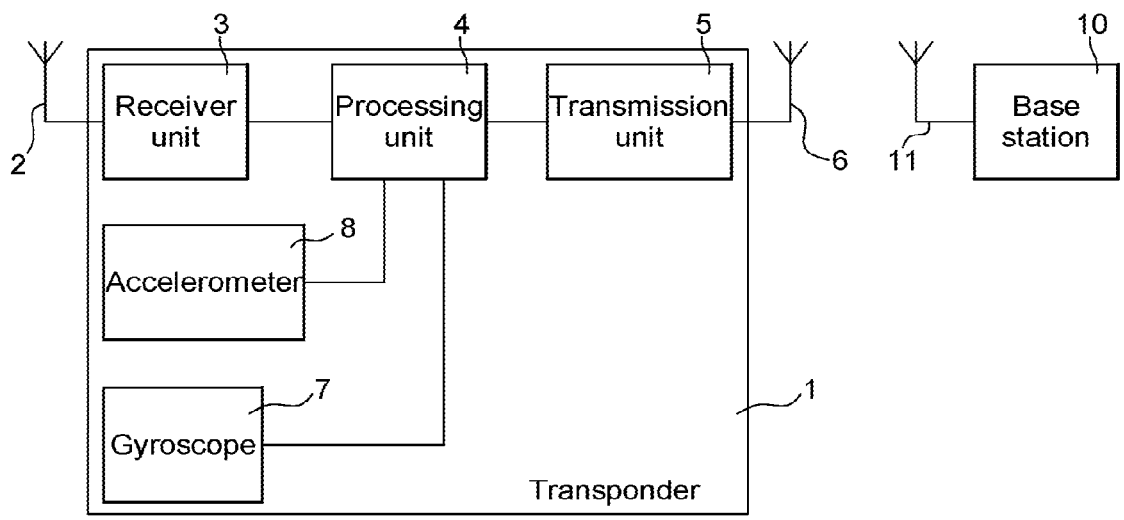
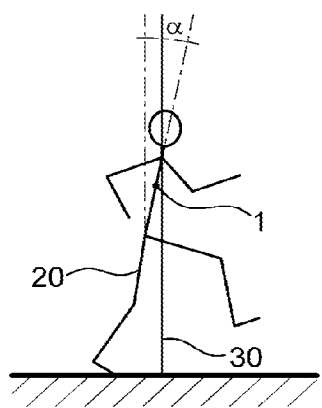
Fig. 2a
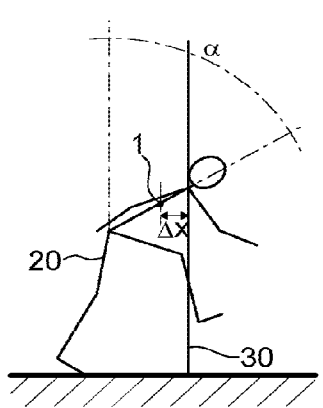
Fig. 2b
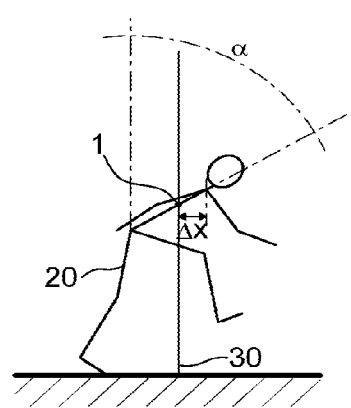
Fig. 2c

SYSTEM FOR MEASURING AND CORRECTING THE FINISH TIME OF AN ATHLETE IN A RACE

This application claims priority from European Patent Application No 15201308.2 of Dec. 18, 2015, the entire disclosure of which is hereby incorporated herein by reference.

FIELD OF THE INVENTION

The invention concerns a system of measuring and correcting the finish time of an athlete in a running race by means of a transponder module fitted to the athlete and preferably carried on an upper part of the athlete's body during the race.

The invention also concerns a method for measuring and correcting the finish time of an athlete in a running race for implementation of the measuring system.

BACKGROUND OF THE INVENTION

During a sports competition, such as a sprint race in athletics, each athlete starts from a starting block. Each athlete is often equipped with a transponder module, which is incorporated in the numbered bib. The time or unofficial race time of the athlete is taken from the reading of the transponder module, which appears when said transponder module crosses the finish line. Afterwards, the official time is judged as a result of the photo finish image in accordance with IAAF Rule 155.2.

It is to be noted that this time must be taken at the moment at which any part of the torso reaches the vertical plane of the nearer edge of the finish line. The official time is normally available approximately 10 to 20 seconds after the unofficial time, which is a long wait for spectators watching said race.

If an athlete crosses the finish line in an upright position, the transponder module is in a position that entirely corresponds to the position for judging the time in the photo finish image. Thus, the error between the unofficial time of the transponder module and the official time taken from the photo finish image differ only according to the inaccuracy of detection of the transponder module. However, many athletes lean forwards when they cross the finish line to obtain an advantage in the photo finish decision. In that case, the athlete is judged shoulders forward in the photo finish image, whereas the transponder module crosses the finish line more than 10 cm behind this finish point. Thus, the difference between the unofficial time of the transponder module and the official time may be considerable. Further, in the case of a close finish between several athletes, the placing of each runner may be erroneous.

In the prior art, and according to the aforementioned time difference between the transponder time and the photo finish time, the unofficial placing is only published when the transponder module time for two athletes differs more than 0.1 seconds. If the difference is smaller, no placing is shown to the spectators until the official photo finish times are available.

CH Patent Application 707401A2 may be cited, which describes a method and a system for the measurement of a time in a sports competition with at least one personalised transponder module. The transponder module can be placed on the competitor or on a movable object accompanying the competitor, for example a cycle or a ski, during the race. The module can be activated either at the start of the race, or at intermediate positions on the race course or at the finish line. A variation in motion is detected by a motion sensor inside the module. The motion measurements can be transmitted from the module to a decoder unit to check a race time. However, there is no description of a correction of a finish time in accordance with measurements made by the motion sensor.

SUMMARY OF THE INVENTION

It is thus an object of the invention to overcome the aforementioned drawbacks of the prior art by proposing a system for measuring and correcting the finish time of an athlete in a running race by means of a transponder module fitted to the athlete and carried on an upper part of the athlete's body during the race.

To this end, the invention concerns a system for measuring and correcting the finish time of at least one athlete in a running race, the measuring system comprising at least one personalised transponder module placed on an upper part of the body of an athlete and a base station, said transponder module comprising a unit for processing data, measurements or commands, a unit for transmitting data and/or measurement and/or command signals, and at least one motion sensor for providing measurement signals to the processing unit, wherein the motion sensor is at least one gyroscope, which is connected to the processing unit in the transponder module, wherein the gyroscope is configured to determine an angle of inclination $\alpha$ of the body of the athlete with respect to a vertical or horizontal direction upon crossing the finish line for a correction of a race finish time, and wherein the processing unit calculates a time error $\Delta t$ for a race time of the athlete based on the angle of inclination $\alpha$ with respect to a vertical or horizontal direction, of the position d of the transponder module with respect to the shoulders of the athlete and the speed v of the athlete at the finish line, the time error being $\Delta t = \Delta x/v$, where $\Delta x = d \cdot \sin(\alpha)$ for an angle of inclination $\alpha$ in a vertical direction or $\Delta x = d \cdot \cos(\alpha)$ for an angle of inclination $\alpha$ in a horizontal direction.

Particular embodiments of the system for measuring and correcting the finish time of an athlete in a track race are defined in the dependent claims 2 to 7.

One advantage of the system for measuring and correcting the finish time lies in the fact that, with the transponder module placed on an upper part of the athlete's body, it is possible to correct the finish time of an athlete after the transponder module crosses the finish line. The transponder module includes at least one motion sensor capable of providing information as to an angle of inclination of the upper part of the athlete's body when crossing the finish line. With the information provided by the transponder module as to the moment of crossing the finish line and the determined angle of inclination, it is possible to estimate the finish time of the transponder module. It is therefore possible to calculate a correction of the unofficial finish time, based on the crossing of the finish line by the transponder module.

Advantageously, the transponder module comprises at least one motion sensor for measuring the angle of inclination of the upper part of the athlete's body. This motion sensor may be an inertial motion sensor. It may be a gyroscope, connected to a processing unit capable of performing calculations based on the gyroscope measurements, in order to transmit information as to the angle of inclination when crossing the finish line. The gyroscope must, in principle, be initially calibrated in order to determine a difference of orientation, i.e. an angle of inclination with respect to a vertical or horizontal direction.

The transponder module is placed on an upper part of the athlete's body, in particular in the numbered bib. Once calibrated and activated, the gyroscope determines the inclination of the athlete at the moment of crossing the finish line in order to correct the unofficial finish time determined and provided by the transponder module with respect to the official time determined with the photo finish image. As a result of the data signal transmitted by the transponder module, a correct unofficial placing of the athletes at the end of the race can be immediately provided at the finish of a track race, for example a sprint race.

To this end, the invention also concerns a method for measuring and correcting the finish time of an athlete in a running race for implementation of the measuring system, wherein the measuring system comprises at least one personalised transponder module placed on an upper part of the body of the athlete and a base station, said transponder module comprising a unit for processing data, measurements or commands, a unit for transmitting data and/or measurement and/or command signals, and at least one motion sensor, which is at least one gyroscope connected to the processing unit in the transponder unit for providing measurement signals to the processing unit, wherein the method includes the steps of:

measuring an angle of inclination α of the athlete by means of the gyroscope of the transponder module activated at the moment of crossing the finish line, correcting a race finish time for the athlete based on the measurement of the angle of inclination α in the transponder unit or in the base station, by effecting a calculation of a time error Δt of a race finish time for the athlete in the processing unit of the transponder module based on the angle of inclination α with respect to a vertical or horizontal direction, of the position d of the transponder module with respect to the shoulders of the athlete and the speed v of the athlete at the finish line, the time error being $\Delta t = \Delta x/v$, where $\Delta x = d \cdot \sin(\alpha)$ for an angle of inclination α in a vertical direction or $\Delta x = d \cdot \cos(\alpha)$ for an angle of inclination α in a horizontal direction.

Particular steps of the measuring method are defined in the dependent claims 9 to 11.

BRIEF DESCRIPTION OF THE DRAWINGS

The objects, advantages and features of the system for measuring and correcting the finish time of an athlete in a running race, and the method for implementation of the measuring system will appear more clearly in the following description of at least one non-limiting embodiment, illustrated by the drawings, in which:

FIG. 1 is a schematic view of the main elements of a system for measuring and correcting the finish time of an athlete in a running race according to the invention;

FIGS. 2a to 2c show schematic views of an athlete, who is provided with a transponder module, showing one view of him crossing a finish line in an upright position and two views with the upper part of his body leaning as he crosses the finish line.

DETAILED DESCRIPTION OF THE INVENTION

Figure 3:
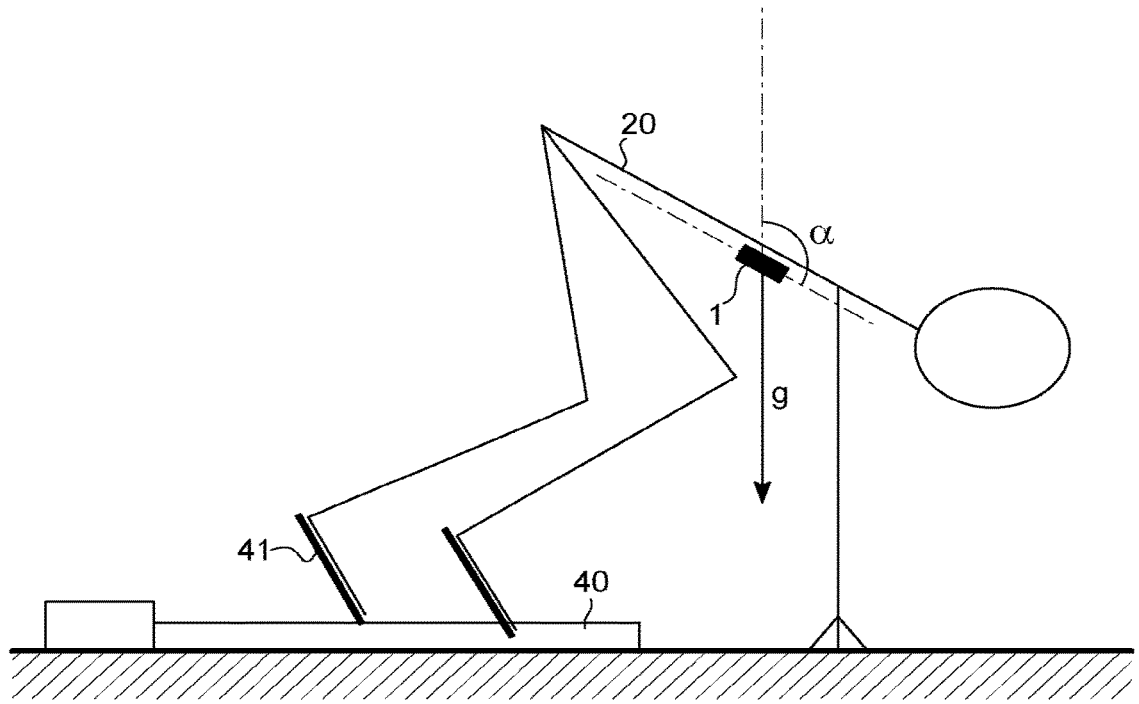
FIG. 3 shows a schematic view of an athlete, who is provided with a transponder module, in the starting position on a starting block.

In the following description, all those elements of the system for measuring and correcting the finish time of an athlete in a running race that are well known to those skilled in the art in this technical field will be described only in a simplified manner. The running race may take place on a track or on a road or in woods or mountains.

FIG. 1 shows a schematic view of the main elements, which form a system for measuring and correcting the finish time of an athlete in a track or road race. To achieve this, the system comprises one or more transponder modules 1 and at least one base station 10 for the communication of data and/or of measurements and/or of commands between transponder module 1 and base station 10. Each transponder module 1 for the competition is placed on a part of the athlete's body, for example in a numbered bib, and is thus personalised or adapted to fit the athlete who wears it. Preferably, transponder module 1 is placed on an upper part of the athlete's body, such as the thorax. As explained below, said transponder module is placed at the centre of gravity, such as the thorax. This makes it possible to detect rotation of the athlete's upper body, particularly at the moment of crossing the finish line, in order to correct the athlete's unofficial race time.

Preferably, at the finish line, there is provided an antenna loop on the ground or a side antenna aligned with the finish line in order to transmit a magnetic field signal. This magnetic field signal may be stationary or with synchronization modulation in specified periods. The transponder module 1 of each athlete in the race can detect the crossing of the finish line by measuring one or more intensities of the magnetic field close to the finish antenna. It is also possible for transponder module 1 to determine a finish time prediction on this basis. A time measurement can also be made in transponder module 1 or via the transmission of field intensity measurement signals to base station 10. It is also possible for transponder module 1 to be awakened and/or synchronized by another antenna at the start or at different points on the race track.

Transponder module 1 may be of the active type with a battery or solar cell or other energy source integrated in the module, or of the passive type, powered by receiving an interrogation signal or conventional wake-up signal. However, where one or more motion sensors are used in the transponder module, it is necessary to have a transponder module of the active type.

Transponder module 1 comprises a wireless signal receiver unit 3 for receiving, via an antenna 2, data or command signals from a base station 10 or from a transmitter placed in a starting block of the measuring system or along the race course or track or also at the finish line. Preferably, the signals received by antenna 2 connected to receiver unit 3 are signals for awakening or synchronizing transponder module 1, which may be in a standby state prior to receiving such signals. These synchronization signals are generated, as indicated above, by base station 10 or by a transmitter in the starting block or along the race track, in particular after the "set" signal of an athletics race or immediately at the moment the starting pistol is fired.

It is to be noted that the transponder module 1 may also not include receiver unit 3, so as to perform measurements using only at least one motion sensor and transmit the information to the base station for correction of the finish time.

Transponder module 1 also comprises a processing unit 4, which may be a state machine, a processor or a microcontroller, for controlling all the data or commands or measurements to be received or transmitted. Said processing unit may also be synchronized as soon as the race starts, if it comprises a time base to allow determination of a race time. The synchronization of transponder module 1 may also be performed at different points on the race or close to the finish line. Processing unit 4 receives the data or commands shaped in receiver unit 3 so as to also awaken all the components that form transponder module 1. Processing unit 4 is also connected to a unit 5 for the transmission of signals via an antenna 6 to base station 10. Base station 10 may be a race timing system and comprises an antenna 11 for signal transmission or reception.

Transponder module 1 further includes at least one motion sensor 7 connected to processing unit 4 to provide measuring signals continuously or intermittently to processing unit 4 once the transponder module has been awakened and/or synchronized. Transponder module 1 may comprise as a motion sensor at least one gyrometer or gyroscope 7. Preferably, gyroscope 7 can determine a rotational speed and an angle of rotation of the upper part of the athlete's body in order to determine an angle $\alpha$ of the upper part of the body, for example, with respect to a direction vertical or perpendicular to the track. Such determination by the gyroscope is obviously only possible if the initial orientation is known. The measurement signals are provided directly to processing unit 4. The angle of inclination $\alpha$ may also be determined with respect to a horizontal direction.

It is to be noted that the motion sensor of transponder module 1 may also be an assembly that comprises a three-axis accelerometer 8, a three-axis gyroscope 7 and a three-axis magnetic sensor (not represented). This assembly defines a 9-axis inertial sensor.

Transponder module 1 may also comprise another motion sensor, which is an accelerometer 8 also connected to processing unit 4. Accelerometer 8 can measure the acceleration of an athlete at the moment of the start of the race and stride rates throughout the race until the finish. Further, gyroscope 7 may be a three-axis gyroscope, as well as accelerometer 8, to perform measurements in the three x, y, z directions.

In transponder module 1, the measurement signals from gyroscope 7 and from accelerometer 8 or from other types of sensors are sampled by processing unit 4 or directly by the actual sensor prior to transmission to processing unit 4. The measurement signals may be directly transmitted to base station 10 using wireless transmission unit 5. However, the measurement signals can be improved, particularly after filtering, and then subsequently stored and/or sent to base station 10. The data from the various sensors and any detection event could also be processed. It would also be possible to process extracted motion features, such as step frequency, and transmit this information to base station 10 in addition to the actual data from accelerometer 8 and from gyroscope 7.

It is also to be noted that the signals received by antenna 2 connected to receiver unit 3 may be low frequency signals of around 125 kHz, whereas the signals transmitted by antenna 6 connected to transmission unit 5 may be relatively high frequency signals, for example HF or UHF signals at a frequency higher than 300 MHz. However, it may be envisaged to have a transponder module 1 with a single transceiver antenna, capable of switching to receive or transmit data signals. In such case, it is preferred to have reception of at least one wake-up signal and transmission of data signals at a similar carrier frequency with FSK, BPSK, QPSK or ON-OFF keying modulation of the transmitted data.

As can be seen in FIGS. 2*a* to 2*c*, an athlete 20 can cross finish line 30 in an upright position, i.e. with a small angle of inclination $\alpha$ of the upper part of the body with respect to the vertical. Transponder module 1 thus crosses at the same time as the upper part of the body as shown in FIG. 2*a*. If an athlete 20 leans forward when he crosses finish line 30, transponder module 1 is still behind at a distance $\Delta x$ from finish line 30, as shown in FIG. 2*b*. Finally, when transponder module 1 crosses the finish line, as shown in FIG. 2*c*, and is detected by the base station of the timing measurement system, it obtains a timestamp. This timestamp is $\Delta x/v$ too late in comparison to the final official time of athlete 20, where v the is the speed of the athlete. For example, for a 100 m sprint race, the speed of athlete 20 is close to 12 m/s on crossing the finish line 30.

With an estimation of the inclination $\alpha$ of the upper part of the body of athlete 20, speed v and the mean position of transponder module 1 on the upper part of the body, it is possible to provide the approximate detection error and to correct it. By way of example, if transponder module 1 is placed at a distance d, for example 25 cm below the shoulders of athlete 20, the inclination $\alpha$ of the upper part of the body can be measured by the gyroscope of transponder module 1 at an angle $\alpha$ of 66°, as shown in FIGS. 2*a* and 2*b*, with a sprint race speed of 12 m/s. This race speed can preferably be calculated in transponder module 1, or in base station 10, at the moment of crossing finish line 30, by the measurements of motion sensors 7, 8.

Distance d can also be estimated on the basis of anthropometric parameters for each athlete. This distance d may also be a function of the height of the athlete. The estimated distance d may also be directly provided with the manufacturer of each race bib. If the angle of inclination $\alpha$ is determined with respect to a vertical direction, the error on the distance at the finish line is $\Delta x = d \cdot \sin(\alpha)$. However, if the angle of inclination $\alpha$ is determined with respect to a horizontal direction, the error on the distance at the finish line is $\Delta x = d \cdot \cos(\alpha)$.

The race time taken by transponder module 1 for an athlete may be equal to 9.598 s. The error on the distance becomes $\Delta x = (25 \text{ cm}) \cdot \sin(\alpha) = 22.8$ cm and the time error $\Delta t = \Delta x/v = 0.019$ s. Thus, the correct finish time would then be 9.579 s, which is rounded up in accordance with the rules of athletics to 9.58 s. This corresponds to the official race time to be communicated, for example, to the spectators of said race more quickly than the correct determination by the photo finish image of the official race time for each athlete 20.

As represented in FIG. 1, at the moment of the start, an athlete 20, who is provided with a transponder module 1, is crouching with both feet resting on two support blocks of a starting block 40, which is placed on and secured to the ground on the track. Preferably, the motion sensor can be a 9-axis inertial sensor. In order to estimate the inclination $\alpha$ of the upper part of the body based on the gyroscope signals, it is necessary to know the initial angle, for example at the start of the race. This angle $\alpha$ can be obtained by measuring the vector of the centre of gravity g by means of a three-axis accelerometer. This initial angle is stored in the transponder module, which must be activated for this measurement at least just before the start. The initial angle is thus stored during the phase after the "set" announcement and before the starting pistol is fired. Once the initial angle is known, the inclination of the upper part of the body can be calculated by operations of rotation based on the gyroscope signals during the race and mainly at the finish line.

It is to be noted that it is necessary to have an initial condition in order to determine angle of inclination α. The transponder module with the motion sensor must be calibrated to be able to make this angle of inclination measurement on the crossing of the finish line. This initial condition can preferably be defined before the start of the race, when the athlete remains ready as shown in FIG. 3, but can also be estimated during the race before the finish line is crossed.

For the race time measurement method for implementation of the measuring system, the angle of the upper part of an athlete's body in a race could be measured in the transponder module. This module can be activated at the start, or in intermediate positions between the start and the finish line, or at the finish. Preferably, the transponder module is activated at the start of the race. The motion sensor, which may comprise at least the gyroscope, is arranged to determine an angle of inclination of the upper part of the body of the athlete, who wears the transponder module. An initial orientation of the transponder module can be defined and stored just before the start of the race. Thus, once the transponder module approaches the finish line and, for example, while detecting low frequency interrogation signals from a finish antenna, the angle of inclination and the time difference can be calculated directly in said transponder module. Once calculated, there may be a transmission of data or command signals to the base station to define a corrected race time. However, it is also possible to transmit only the angle of inclination measured in the transponder module, with the time difference calculation performed directly after the crossing of the finish line by the base station.

It is to be noted that the activated transponder module may also transmit all the data and measurements made by its sensors to the base station, which, in that case, determines and calculates the time difference and the unofficial time correction for each athlete.

From the description that has just been given, several variants of the system and method for measuring and correcting the finish time of an athlete in a race can be devised by those skilled in the art without departing from the scope of the invention defined by the claims. Several transponder modules could be provided on a part of the athlete's body for determination of the angle of inclination on crossing the finish line and correction of the unofficial finish time.

What is claimed is:

1. A system for measuring and correcting a finish time of at least one athlete in a running race, the measuring system comprising:
    at least one personalized transponder module placed on an upper part of a body of an athlete;
    and a base station, wherein
    said transponder module comprising circuitry to process data, measurements or commands, a transmitter of data and/or measurement and/or command signals, and at least one motion sensor to provide measurement signals to the processing circuitry,
    wherein the motion sensor is at least one gyroscope, which is connected to the processing circuitry in the transponder module,
    wherein the gyroscope is configured to determine an angle of inclination α of the body of the athlete with respect to a vertical or horizontal direction upon crossing a finish line for a correction of a race finish time, and
    wherein the processing circuitry is configured to calculate a time error Δt for a race time of the athlete based on the angle of inclination α with respect to the vertical or horizontal direction, a position d of the transponder module with respect to shoulders of the athlete, and a speed v of the athlete at the finish line, the time error being Δt=Δx/v, where Δx=d·sin(α) for an angle of inclination α in the vertical direction or Δx=d·cos(α) for an angle of inclination α in the horizontal direction.

2. The measuring system according to claim 1, wherein the transponder module further includes another motion sensor, which is an accelerometer connected to the processing circuitry to detect a variation in motion of said module or a vibration level of said module.

3. The measuring system according to claim 2, wherein the gyroscope is a three-axis gyroscope, and wherein the accelerometer is a three-axis accelerometer.

4. The measuring system according to claim 1, wherein the motion sensor is a 9-axis inertial sensor, which comprises an assembly with a three-axis accelerometer, a three-axis gyroscope and a three-axis magnetic sensor.

5. The measuring system according to claim 1, wherein the gyroscope is configured to be calibrated at a start of a race.

6. The measuring system according to claim 1, wherein the processing circuitry is configured to determine a race time for the athlete corrected in the transponder module to transmit a correct race time for the athlete to the base station.

7. The measuring system according to claim 1, wherein the transponder module further includes a wireless signal receiver to receive via an antenna data or command signals from the base station or from a transmitter arranged at a start of the race or along a race course.

8. A method for measuring and correcting the finish time of an athlete in a running race for implementation of the measuring system according to claim 1, wherein the measuring system comprises the at least one personalized transponder module placed on the upper part of the body of the athlete, and the base station, said transponder module comprising the circuitry to process data, measurements or commands, the transmitter of data and/or measurement and/or command signals, and the at least one motion sensor, which is the at least one gyroscope connected to the processing circuitry in the transponder module to provide measurement signals to the processing circuitry, wherein the method comprises:
    measuring the angle of inclination α of the athlete by the gyroscope of the transponder module activated at a moment of crossing the finish line, and
    correcting the race finish time for the athlete based on the measurement of the angle of inclination α in the transponder module or in the base station, by effecting a calculation of the time error Δt of the race finish time for the athlete in the processing circuitry of the transponder module based on the angle of inclination α with respect to the vertical or horizontal direction, the position d of the transponder module with respect to the shoulders of the athlete, and the speed v of the athlete at the finish line, the time error being Δt=Δx/v, where Δx=d·sin(α) for the angle of inclination α in the vertical direction or Δx=d·cos(α) for the angle of inclination α in the horizontal direction.

9. The measuring method according to claim 8, wherein, once activated, an acceleration measurement of the athlete is performed by another motion sensor, which is an accelerometer of the transponder module in order to detect a variation in motion of said module or a vibration level of said module.

10. The measuring method according to claim 8, wherein the transponder module is synchronized at a start of the race or at different points on a course or close to the finish line by an interrogation or wake-up signal.

11. The measuring method according to claim 10, wherein once activated and synchronized, the transponder module determines a corrected race finish time on the crossing of the finish line based on intensity measurements of a magnetic field signal from an antenna close to the finish line and captured by a receiver, and wherein the corrected race finish time is transmitted from the transponder module to the base station.

\* \* \* \* \*